US011890079B1

(12) United States Patent
Sandgaard

(10) Patent No.: US 11,890,079 B1
(45) Date of Patent: *Feb. 6, 2024

(54) METHOD AND APPARATUS FOR NON-INVASIVELY DETECTING BLOOD VOLUME IMBALANCES IN A MAMMALIAN SUBJECT

(71) Applicant: Zynex Monitoring Solutions Inc., Englewood, CO (US)

(72) Inventor: Thomas Sandgaard, Castle Rock, CO (US)

( * ) Notice: Subject to any disclaimer, the term of this patent is extended or adjusted under 35 U.S.C. 154(b) by 286 days.

This patent is subject to a terminal disclaimer.

(21) Appl. No.: 17/156,573

(22) Filed: Jan. 23, 2021

Related U.S. Application Data

(63) Continuation of application No. 16/198,834, filed on Nov. 22, 2018, now Pat. No. 10,898,082, which is a
(Continued)

(51) Int. Cl.
*A61B 5/02* (2006.01)
*A61B 5/0205* (2006.01)
(Continued)

(52) U.S. Cl.
CPC ...... *A61B 5/02042* (2013.01); *A61B 5/02055* (2013.01); *A61B 5/4848* (2013.01);
(Continued)

(58) Field of Classification Search
None
See application file for complete search history.

(56) References Cited

U.S. PATENT DOCUMENTS

| | | | |
|---|---|---|---|
| 2003/0191395 A1* | 10/2003 | Bowman | G16H 50/50 702/19 |
| 2005/0038345 A1* | 2/2005 | Gorgenberg | A61B 5/0265 600/502 |

(Continued)

*Primary Examiner* — Etsub D Berhanu
(74) *Attorney, Agent, or Firm* — Sheridan Ross P.C.

(57) ABSTRACT

Noninvasive methods and apparatus for detecting blood volume imbalances in a mammalian subject are disclosed. The method includes obtaining baseline measurements of at least three physiological parameters from a subject wherein the parameters are selected from the group consisting of heart rate, electrical body impedance, skin temperature, perfusion index, peripheral blood flow and skin humidity. Measurements of electrical body impedance, skin temperature, perfusion index, peripheral blood flow and skin humidity are taken at one or more extremities of the subject such as the calf, ankle, forearm, thigh, fingers and toes. The physiological parameters for which baseline measurements were obtained are then monitored to detect changes from the baseline measurements that indicate blood volume imbalances. A preferred embodiment comprises computing a baseline blood volume index from the baseline value measurements of each parameter to be monitored and then carrying out the step of monitoring by obtaining real time (current) value measurements of these parameters which are inputted into an algorithm which computes a real time (current) blood volume index based upon the differences between the baseline and real time (current) value measurements.

20 Claims, 10 Drawing Sheets

THE BVM MEASURED PARAMETER CHARACTERISTICS ASSOCIATED TO CONTINUOUS BLOOD LOSS.

THE BVM ALGORITHM PROCESSOR OUTPUT OF MEASURED PARAMETERS IN AN ALARM SCENARIO.

Related U.S. Application Data continuation of application No. 14/160,545, filed on Jan. 21, 2014, now Pat. No. 10,136,822.

(60) Provisional application No. 61/754,912, filed on Jan. 21, 2013.

(51) Int. Cl.
*A61B 5/00* (2006.01)
*A61B 5/026* (2006.01)
*A61B 5/0531* (2021.01)

(52) U.S. Cl.
CPC .......... *A61B 5/6826* (2013.01); *A61B 5/6829* (2013.01); *A61B 5/746* (2013.01); *A61B 5/7425* (2013.01); *A61B 5/026* (2013.01); *A61B 5/0531* (2013.01); *A61B 5/443* (2013.01); *A61B 5/7435* (2013.01); *A61B 2505/05* (2013.01); *A61B 2562/029* (2013.01)

(56) References Cited

U.S. PATENT DOCUMENTS

| | | | | |
|---|---|---|---|---|
| 2005/0203428 | A1* | 9/2005 | Judy | A61B 5/0535 600/506 |
| 2010/0305412 | A1* | 12/2010 | Darrah | A61B 5/7475 600/301 |
| 2012/0016246 | A1* | 1/2012 | Sandgaard | A61B 5/024 600/481 |
| 2012/0296219 | A1* | 11/2012 | Chon | A61B 5/02042 600/479 |

* cited by examiner

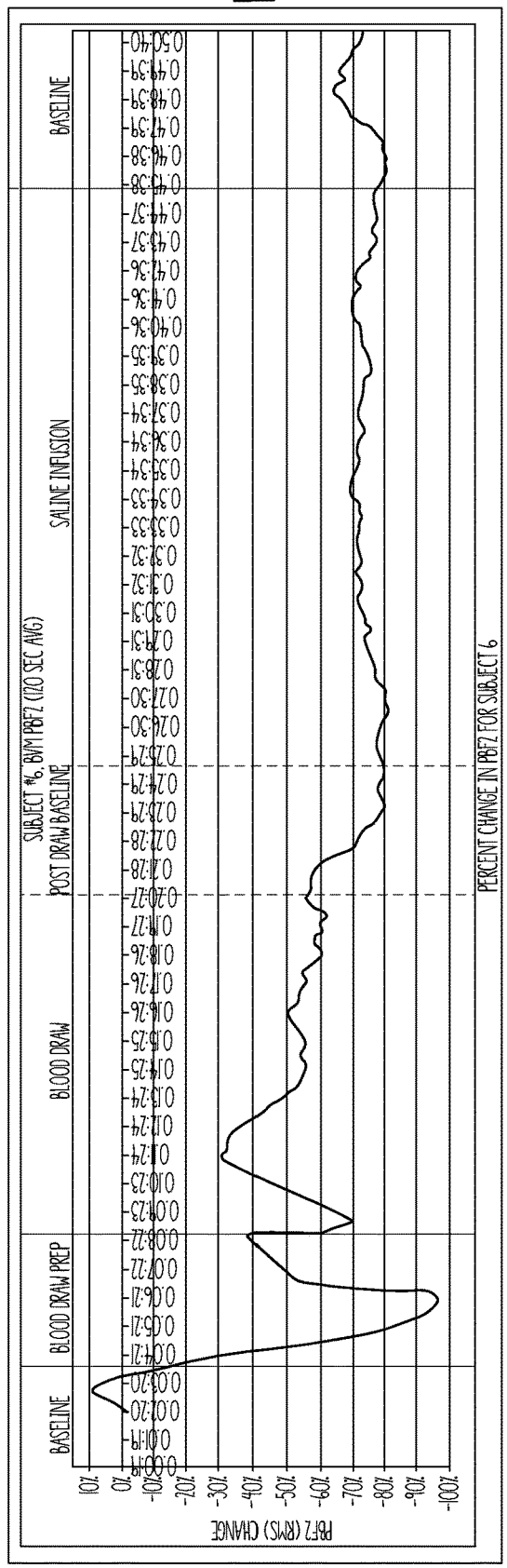
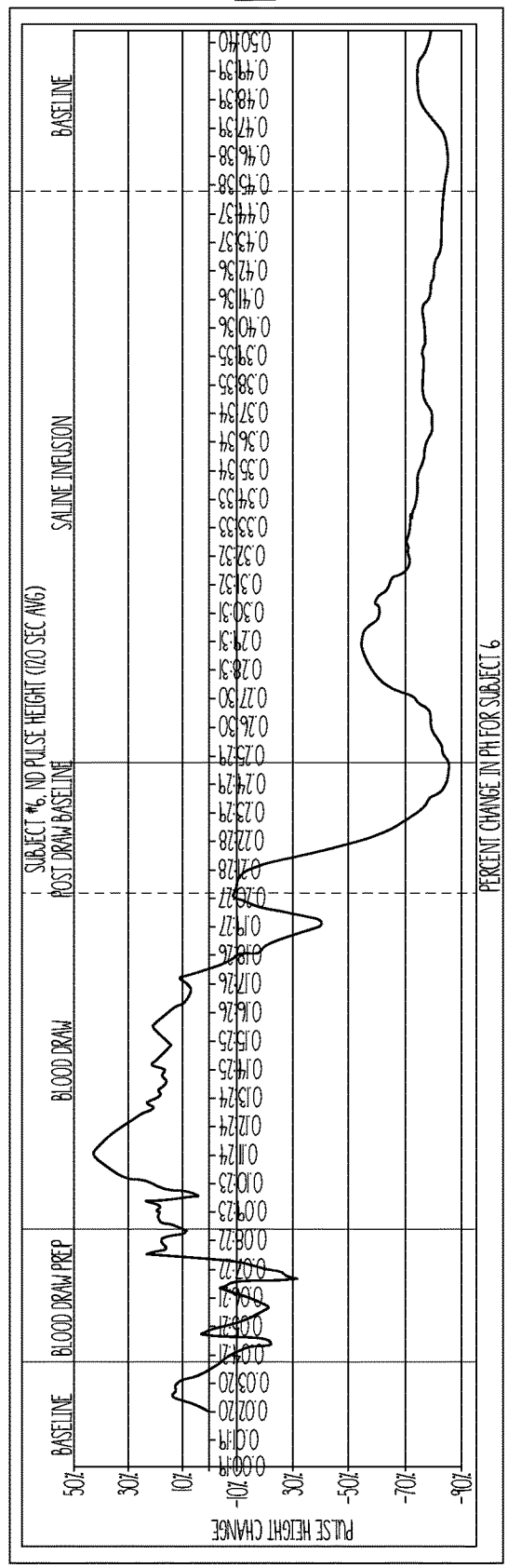

US 11,890,079 B1

METHOD AND APPARATUS FOR NON-INVASIVELY DETECTING BLOOD VOLUME IMBALANCES IN A MAMMALIAN SUBJECT

CROSS REFERENCE TO RELATED APPLICATION

This application is a nonprovisional application claiming the benefit under 35 USC 119(e) of U.S. provisional application No. 61/754,912, filed on Jan. 21, 2013.

TECHNICAL FIELD

The present invention relates generally to systems, methods and apparatus for detecting blood volume imbalances and, more particularly, to non-invasive systems, methods and apparatus for the early detection of blood loss in a patient (which often occurs during and after surgery) to enable clinicians to quickly respond quickly to such indications so that cardiovascular collapse in the patient can be prevented.

BACKGROUND OF THE INVENTION

Undetected or delayed evaluation of a bleeding patient which sometimes occurs during and after surgery is extremely dangerous and may cascade into hemorrhagic shock and result in irreversible or delayed cellular and organ damage and death. In view of this serious problem, it would be desirable if a system and method were available with the ability to continuously and non-invasively detect changes in central blood volume. Such a system would better enable early medical management of patients at high risk for acute blood loss in surgical, post-operative and trauma care settings. National average rates reported in 2011 Patient Safety Indicators (PSI's), categorized as post-operative hemorrhaging or hematoma, were trending at only 3.40 per 1,000 (0.34%) as reported via the Agency for Healthcare Research and Quality (AHRQ). However, clinical data of "high risk" surgical procedures have reported up to 11% postoperative bleeding.[4] Each year in the USA more than 640,000 patients undergo open heart surgery and 0.3% to 11% (19,000 to 70,000) patients develop excessive bleeding postoperatively. About 5% percent of these open heart patients require re-exploration and revisions for bleeding. In the emergency setting, hemorrhage is responsible for over 40% of deaths within the first 24 hours after a traumatic injury.

Current methods for non-invasive monitoring of blood volume loss include vital signs monitoring of heart rate, blood pressure, respiration and oxygen saturation. This "vital signs" approach has not been shown to reliably detect small amounts of acute blood loss[1,2,3]. Invasive methods include central venous and arterial catheters designed to monitor hemodynamic status centrally (e.g. swan-ganz, wedge pressure measurements) but can create insertion complications such as perforations in the vasculature, pneumothorax, arrhythmias, thrombosis and infection. While invasive central monitoring may provide extremely accurate information, applications to trauma and postoperative settings are limited. The early detection and accurate evaluation of blood volume is clinically documented as having a direct influence on improving patient outcomes[5,6]. Data supports the need for blood volume monitoring of patients in the intraoperative, postoperative and trauma settings. Through early detection of acute and progressive blood loss, clinicians may be able to reduce incidences of morbidity and mortality associated with hemorrhagic shock while also reducing the cost of patient care. The study of non-invasive techniques for detecting early blood loss is again emerging in modern literature; however, at this time no such device is available commercially[7,8].

SUMMARY OF THE INVENTION

The present invention provides methods, systems and apparatus for detecting changes in blood volume related parameters which indicate central blood volume changes typically bleeding which occurs during hemorrhagic events.

In a preferred method of the present invention, effective early detection of between 10 and 20% blood loss in a subject/patient can be achieved by measuring and monitoring as few as three of the subject's physiological parameters. These parameters include heart rate, electrical body impedance (bioimpedance), skin temperature, perfusion index, peripheral blood flow and skin humidity.

Bioimpedance is a preferred parameter because it has been shown that bioimpedance increases during blood loss when measured at a patent's extremity. Similarly, heart rate increases during blood loss to maintain blood pressure. Peripheral blood flow is another preferred parameter since the amplitude of arterial blood flow through peripheral extremities particularly the fingers and toes has been shown to decrease during blood loss. Skin temperature is another preferred parameter as skin temperature at peripheral extremities also often decreases during blood loss even though core body temperature is typically maintained during blood loss. In addition, skin humidity manifested as clamminess or sweating has also been shown to increase during blood loss and can be measured by measuring changes in the skin's conductance caused by the increase in skin humidity. Other parameters such as perfusion index are also believed to change with blood loss. Any single parameter on its own is often not sufficient to consistently indicate blood loss. However, the combination of at least three parameters and in a preferred embodiment five parameters, makes the method very reliable.

This preferred method includes obtaining baseline measurements of these parameters (i.e. measurements taken while the patient is resting in the supine position) from the subject which (with the exception of the subject's heart rate) are taken at one or more extremities of the subject, preferably the subject's forearm or calf. The selected parameters are then monitored to detect changes from the baseline measurements that indicate blood loss and other imbalances, typically bleeding.

In a more preferred embodiment of the method of the present invention which uses multiple parameter readings collected via non-invasive sensors placed on a patient's extremities, the system computes and displays a real-time blood volume BVM Index based on relative changes to baseline physiologic values. In this method, a baseline blood volume index is computed from the baseline value measurements of each parameter to be monitored. Real time value measurements of the parameters are then obtained from which a real time blood volume index is computed by inputting the baseline and real time values into an algorithm based upon the differences or changes between the baseline and real time value measurements.

The real time blood volume index is then monitored (either automatically or manually) to determine whether a predetermined blood volume index threshold (typically set between 10 and 20% of the subject's total blood volume (TBV)) is reached which indicates a strong likelihood of bleeding.

An apparatus or system for noninvasively detecting blood volume imbalances in a mammalian subject estimating a blood volume of a mammalian subject is also provided. The apparatus comprises a number of noninvasive sensors which are communicable with the subject to obtain baseline and real time (current) physiologic measurements from the subject. In addition, at least one integrated circuit is provided which is operably connected with the sensors and configured to i) compute baseline and real time (current) blood volume indexes from the physiologic measurements wherein the blood volume indexes are derived from at least three physiological parameters selected from the group consisting of heart rate, electrical body impedance, skin temperature, perfusion index, peripheral blood flow and skin humidity and wherein measurements of electrical body impedance, skin temperature, perfusion index, peripheral blood flow and skin humidity are taken at one or more extremities of the subject, and ii) use the baseline and real time (current) blood volume indexes to generate an output indicative of the current estimated blood volume of the subject which in turn can be monitored to detect blood volume imbalances in the subject.

BRIEF DESCRIPTION OF THE DRAWINGS

The invention will be more readily understood by reference to the accompanying drawings wherein like reference numerals indicate like elements, and wherein reference numerals sharing the same last two digits identify similar corresponding elements throughout the various disclosed embodiments, and in which:

FIG. 8 is a graph showing percent change in PBF2 for subject 6 of the study;

FIG. 9 is a graph showing percent change in PH for subject 6 of the study;

DETAILED DESCRIPTION OF PREFERRED EMBODIMENTS

In a recently conducted study, ten healthy subjects (n=10) were evaluated during a single-unit (450-500 ml) blood draw (which is approximately 10% of the average individual's total blood volume which is about 5 liters) followed by saline infusion (1000-1500 ml). Several physiologic parameters were continuously monitored (1 Hz) for consideration of inclusion and weighting in the BVM Index algorithm. Each parameter was evaluated independently for trends corresponding to manual hemodynamic fluid changes in the subjects. The real-time values of each parameter were then input into various equations of the BVM Index algorithm for assessment of feasibility to detect incremental blood loss. The initial rudimentary algorithm of the BVM Index detected both blood loss and saline infusion in 6 of 9 (67%) subjects reaching >450 ml in blood loss.

Materials and Methods

Subjects. Ten healthy adult volunteers (age range 20-44) participated in a single-unit manual blood draw followed by saline infusion. Only one visit per subject was required and duration of involvement ranged from 2 to 4 hours. All subjects were briefed on research information and potential risks of the study prior to completing informed consent. Inclusion and exclusion criteria were verified followed by a health assessment screening, vital signs measurement and provision of oral fluids. No restrictions were placed on subjects activities of daily living prior to the study participation. A total hemoglobin of at least 10 g/dL (Hematocrit 30%) was confirmed before blood withdraw was started.

Figure 1:
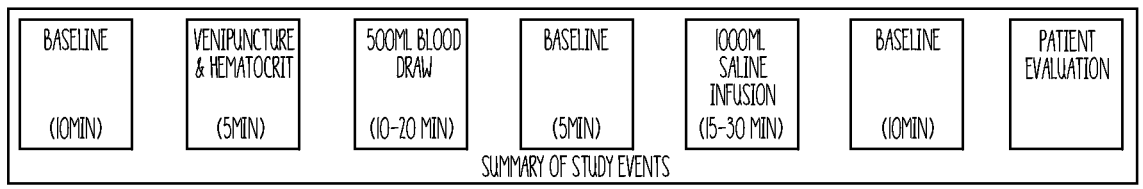
FIG. 1 is a block diagram providing a summary of the study events.

Protocol. While resting in a supine position, subjects were instrumented with non-invasive physiologic sensors for the investigational device and remained at rest for the remainder of study activities. The primary events of the study included an initial baseline period, venipuncture and hemoglobin measurement, 500 ml blood draw, and 1000 ml saline infusion. Additional baseline measures were taken after blood draw and saline infusion as shown in FIG. 1. Attempts were made to collect 450-500 ml of blood from the median cubital vein of the right arm using a 16 gauge needle and gravity drain. Blood pressure and EKG were monitored by the medical staff throughout the study. Measurements for each physiological parameter of interest were monitored continuously (1 Hz sample rate) throughout the study period and streamed to a PC data collection system for post analysis.

Figure 2:
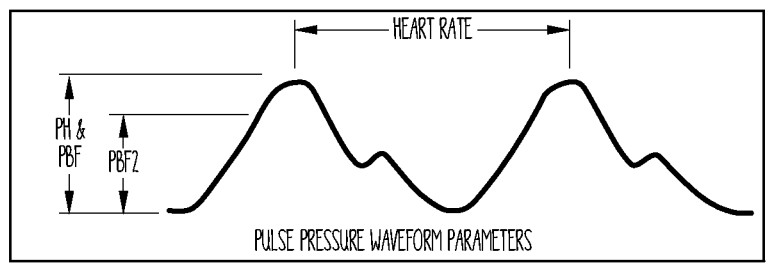
FIG. 2 is graph showing the pulse pressure waveform parameters.

Parameters Measured. During this study, the BVM actively measured regional bioimpedance (BI), heart rate (HR), peak-to-peak amplitude of the peripheral blood flow (PBF) and root mean square amplitude of the peripheral blood flow (PBF2). Bioimpedance was measured along the left calf using four adhesive ECG type electrodes. A photoplethysmograph sensor placed on the subjects left index toe measured blood changes in peripheral blood flow. These sensors measure the surge of blood through the vasculature as the pulse pressure wave changes. This pulse pressure waveform (FIG. 2) is analyzed to calculate heart rate and the various measures of peripheral blood flow amplitude.

Figure 3:
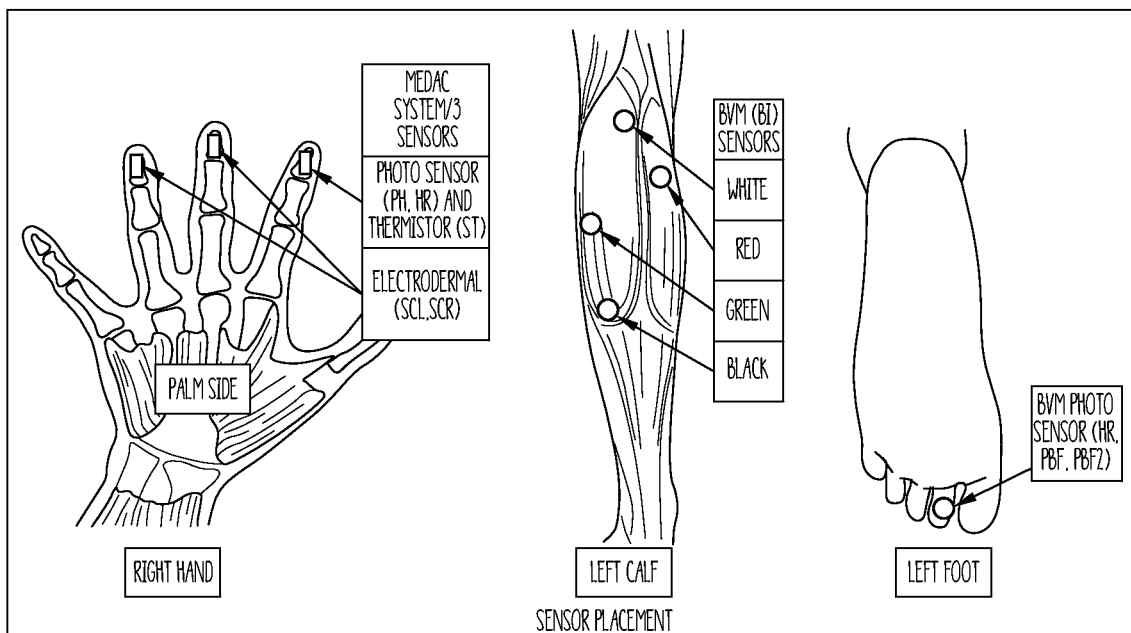
FIG. 3 illustrates side views showing the placement of sensors of the system of the present invention on the right hand, left calf and left foot.

A second commercially available accessory system, MEDAC System/3 biofeedback device with 510(k) number K914925, was used to actively measure electrodermal activity, skin temperature (ST) and respiration (R) changes stimulated by sympathetic nervous system response to stress. Two principal measures of electrodermal activity were monitored by gold-plated electrodes placed on adjacent finger tips of the right hand; 1) skin conductance level (SCL) measuring tonic sensory receptors that adapt slowly to a stimulus and 2) skin conductance response (SCR) measuring phasic receptors that adapt rapidly to a stimulus. These electrodermal responses are associated with the activity of eccrine sweat glands which increase the conductivity of the skin. The skin temperature was measured by a thermistor on a finger tip of the subjects right hand and respiration was measured by a pressure transducer belt placed around the waist at the diaphragm. The MEDAC system also included capabilities to monitor heart rate (HR) and a variation of pulse wave amplitude (PH) with a different photoplethysmograph sensor and unique software algorithm so duplicate measures for these parameters were recorded for comparison to the BVM data. This sensor was also placed on a finger of the right hand. A summary of parameters measured and sensor placement is illustrated in FIG. 3.

Figure 4:
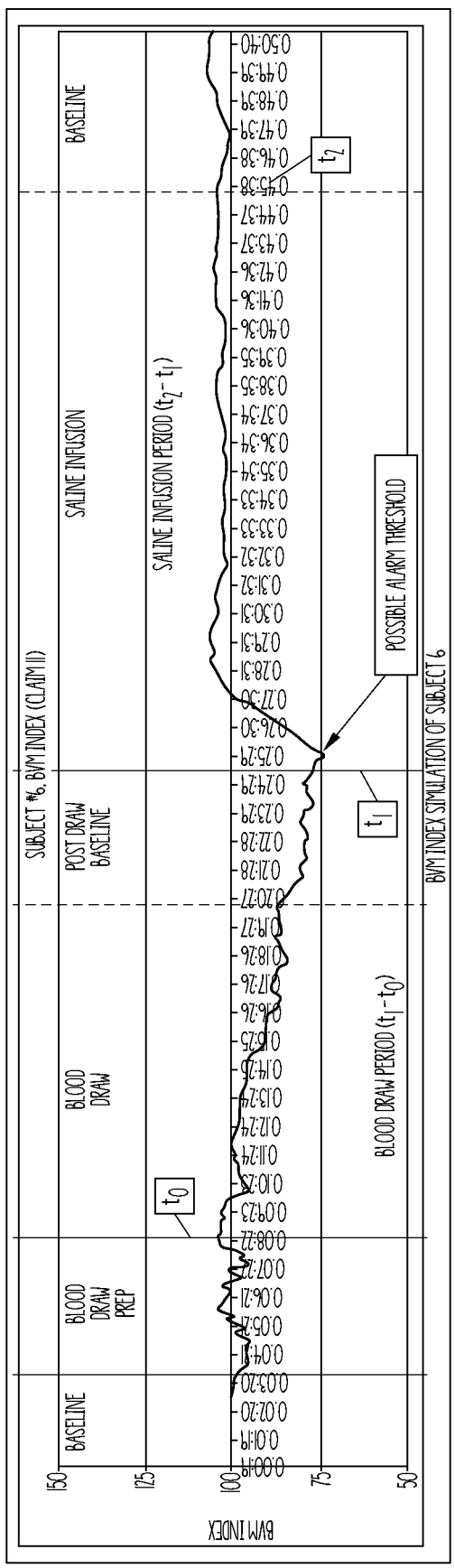
FIG. 4 is graph showing the BVM Index simulation of subject 6 of the study.

BVM Index. One important object of the study was to compute a BVM Index so that the clinician can be alerted at early thresholds of circulatory compromise suspected from progressive bleeding. The BVM Index will be computed by an algorithm that compares the time of interest (typically the current or real time) to a baseline value. Initial equations for the BVM Index are defined in US Patent Application 20120016426 which is hereby incorporated by reference and data from clinical studies will be used to refine the equation that will be used in the commercialized system. The starting value of the BVM Index will be 100, after which the value will change based on sensor input changes from physiological response of the patient to his/her clinical status. Each parameter measured will be expressed as percent change relative to baseline values and will have a unique weighting in the equation. The simulation of the BVM Index from subject 6 (>10% TBV loss) is illustrated in FIG. 4. Note the decline in BVM Index during blood draw period.

The most current algorithm for computing the BVM Index (BVI) is as follows:

$$BVI = (100*(1-(((BI_{Normalized}-BI_{Baseline})/BI_{Baseline}) \\ *BI_{Coefficient})-(((HR-HR_{Baseline})/ \\ HR_{Baseline}*HR_{Coefficient})+(((PBF-PBF_{Baseline})/ \\ PBF_{Baseline}*PBF_{Coefficient})-(((GSR-GSR_{Baseline})/ \\ GSR_{Baseline}*GSR_{Coefficient})+(((STemp- \\ STemp_{Baseline})/STemp_{Baseline}*STemp_{Coefficient})))$$

Where,
BI=Peripheral Bioimpedance (forearm or calf)
HR=Heart Rate
PBF=Peripheral Blood Flow
GSR=Galvanic Skin Response
Stemp=Skin Temperature (investigating temperature gradient, measuring forearm vs finger or calf vs toe, when temperature diverge past threshold higher risk of mortality)
$BI_{Normalized}$=Peripheral Bioimpedance normalized by removing known physiological drift (~3% per hr for 1st hour after postural shift from standing to supine position)
$BI_{Coefficient} = 0.725$
$HR_{Coefficient} = 0.145$
$PBF_{Coefficient} = 0.043$
$GSR_{Coefficient} = 0.014$
$STemp_{Coefficient} = 0.072$

|  | Signal Averaging | Coefficient Weighting | Coefficient Fraction |
|---|---|---|---|
| BI | 17 sec | 5 | 0.725 |
| HR | 240 sec | 1 | 0.145 |
| PBF | 360 sec | 0.3 | 0.043 |
| GSR | 360 sec | 0.1 | 0.014 |
| STemp | 360 sec | 0.5 | 0.072 |
| Total |  | 6.9 | 100% |

Results

Data for all parameters was successfully collected on all 10 subjects for the duration of the study. Only 1 subject failed to reach a 450 ml blood draw (subject 5, 155 ml after 18 min) and therefore this data was omitted from summary analysis. Gross values for % change during blood draw period are provided in Table 1. Significant data was also collected during 1000 mL of saline infusion but is not presented here as physiologic effects from blood loss are the primary focus for this initial report.

TABLE 1

Subject Information

| n | Gender | Age | Ht | Wt (lbs) | BMI | Est. TBV (L) | Blood Removed (ml) | % TBV | Time (mm:ss) |
|---|---|---|---|---|---|---|---|---|---|
| 1 | M | 44 | 6'2" | 235 | 30.2 | 8.3 | 500 | 6.02% | 9:26 |
| 2 | F | 33 | 5'2" | 160 | 29.3 | 5.56 | 480 | 8.63% | 13:10 |
| 3 | F | 21 | 5'8" | 260 | 39.5 | 8.9 | 500 | 5.62% | 10:31 |
| 4 | M | 21 | 5'4" | 165 | 28.3 | 6.01 | 500 | 8.32% | 8:51 |
| 5 | F | 28 | 5'2" | 195 | 35.7 | 6.72 | 155 | 2.30% | 18:05 |
| 6 | F | 22 | 4'11" | 135 | 27.3 | 4.72 | 484 | 10.25% | 12:00 |
| 7 | F | 31 | 5'3" | 160 | 28.3 | 5.57 | 510 | 9.16% | 14:27 |
| 8 | M | 21 | 6'1" | 200 | 26.4 | 7.18 | 505 | 7.03% | 7:42 |
| 9 | F | 33 | 5'8" | 165 | 25.1 | 5.75 | 480 | 8.35% | 17:53 |
| 10 | F | 20 | 5'2" | 205 | 37.5 | 7.05 | 500 | 7.09% | 9:10 |

All values for the blood draw period described subsequently were measured between "Baseline-Stop" to "Saline-Infusion-Start" for consistency (FIG. 4). Also, % TBV (total blood volume) removed was calculated for each subject using Nadler's formula for correlation to parameters measured. Additionally, real-time data streaming (1 Hz) enabled us to identify potential sources of artifact error and transient shifts in measured parameters. Upon inspection of the data from subjects one, eight and ten (1,8,10) potential sources of significant error were exhibited during blood volume loss and were therefore omitted from subsequent correlation results presented. A summary of the data for the subjects is set forth below in Table 2.

TABLE 2

% of Parameters Measured (450-500 ml blood draw) Raw Values

| | | BVM | | | | MEDAC | | | | | |
|---|---|---|---|---|---|---|---|---|---|---|---|
| Subjects | | | | | | | | | | | |
| n | % TBV Removed | % BI (17sec avg) | % HR (120 sec avg) | % PBF (17sec avg) | % PBF2 (120 sec avg) | % HR (120 sec avg) | % PH (120 sec avg) | % SCR (120 sec avg) | % SCL (120 sec avg) | % ST (120 sec avg) | % R (120 sec avg) |
| 1 | 6.0% | 6.95% | 4.22% | −18.23% | −0.36% | 1.55% | −8.32% | 0.00% | −1.25% | 0.32% | 0.02 |
| 2 | 8.6% | 2.36% | −3.91% | −6.41% | −14.28% | 21.34% | −26.60% | 8.62% | −19.19% | 1.10% | 0.07 |
| 3 | 5.6% | 1.92% | 7.66% | −61.08% | −53.72% | 1.84% | −61.40% | −28.70% | 20.25% | −0.52% | 0.15 |
| 4 | 8.3% | 1.80% | −4.11% | 6.50% | 1.36% | −4.41% | −33.09% | −8.90% | −0.79% | −0.17% | — |
| 5 | 2.3% | | | | | | | | | | |
| 6 | 10.3% | 4.63% | 21.59% | −47.92% | −76.37% | 16.70% | −85.45% | −11.02% | 66.08% | 2.39% | 0.18 |
| 7 | 9.2% | 3.84% | 0.64% | −19.10% | −19.61% | 5.11% | −40.98% | −8.80% | 2.53% | −0.86% | — |
| 8 | 7.0% | 5.18% | 8.55% | 325.70% | 379.64% | 7.88% | −20.63% | 18.32% | 133.33% | 1.70% | — |
| 9 | 8.4% | 3.42% | −16.74% | 56.25% | 29.60% | 11.52% | 14.63% | −26.24% | −26.70% | −2.95% | 0.04 |
| 10 | 7.1% | 4.35% | −2.64% | −3.70% | 22.89% | 13.00% | 37.90% | −10.58% | 17.52% | 1.93% | 0.02 |

Bioimpedance (BI). Regional bioimpedance measured across the calf detects intravascular fluid changes and as blood flow to the extremity is reduced through vasoconstriction and BI was expected to increase. Bioimpedance correlation to cardiovascular health and status change in subjects has been well explored; however, the instant approach is believed to be unique[9-18]. In this study, the measured BI over the blood draw period increased for all subjects reaching >450 ml blood draw by a mean of 3.8% (range 0.17 to 0.87 ohms). Conversely, BI generally decreased by a mean of −1.82% (range 0.16 to −0.63 ohms) for the same group of subjects after saline infusion which serves as confirmation of the ability to monitor subtle intravascular fluid changes with the device/system of the present invention.

Figure 5:
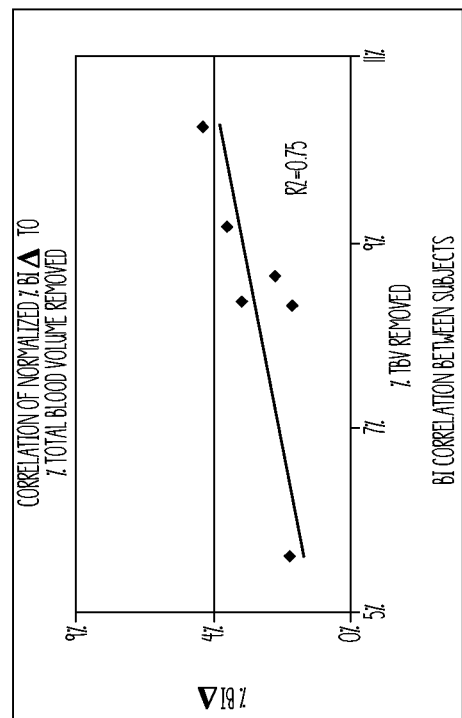
FIG. 5 is a graph showing BI correlation between subjects of the study.
Figure 6:
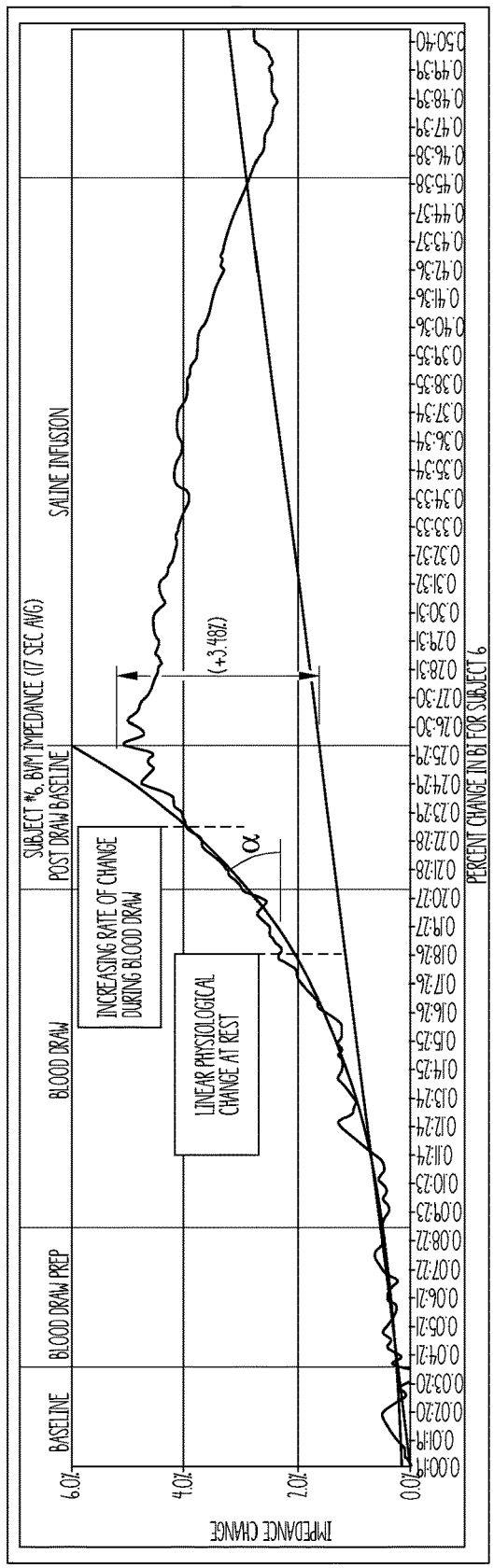
FIG. 6 is a graph showing percent change in BI for subject 6 of the study.

Initial correlation results between subjects (inter-subject) suggest a moderately strong relationship between % TBV removed and % ΔBI may exist ($R^2=0.75$) as illustrated in plot of FIG. 5. In this study no provisions were made to collect discrete time points for each 100 ml of blood removal (intra-subject) which limits further correlation analysis at this time. Also, it is well documented that tolerance to <500 ml blood loss and onset of accompanying symptoms is highly variable among subjects[1-3,6,20]. This prompted a deeper analysis of % ΔBI trends for subjects with the greatest % TBV removed. In both subjects with >9% TBV removed, a greater rate of change in % ΔBI can be observed at later stages of the blood draw. Both the linear nature of baseline values and increasing rate of change in % ΔBI for subject 6, who had the largest % TBV removed, is shown in FIG. 6.

Figure 7:
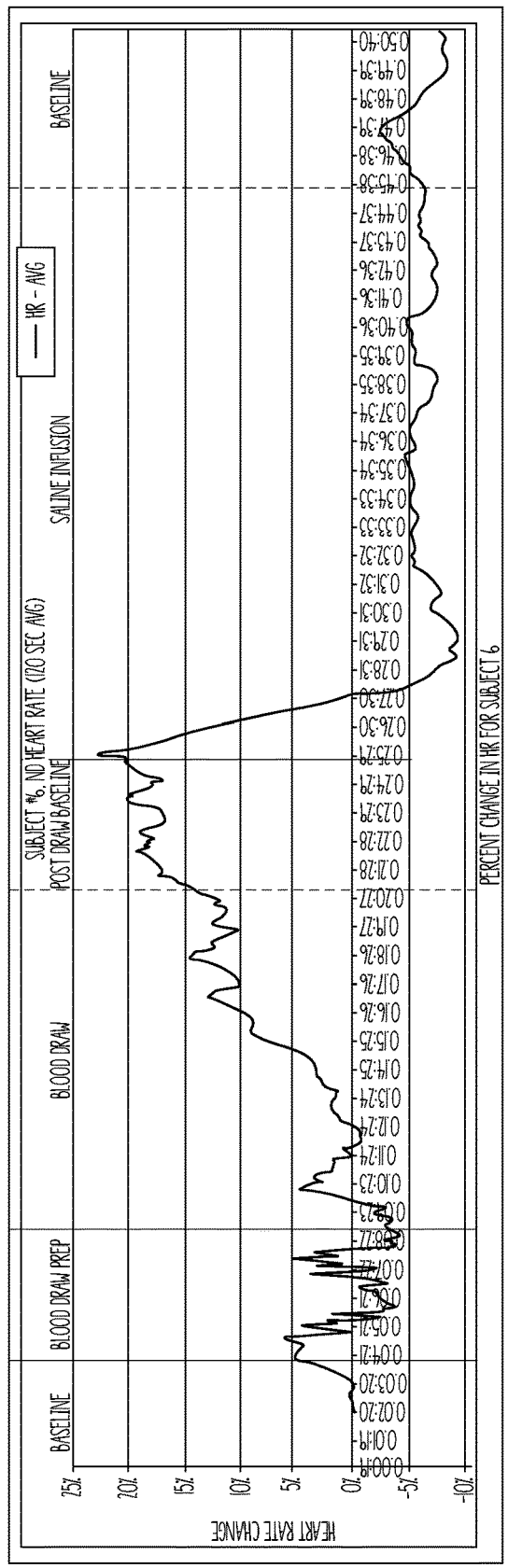
FIG. 7 is a graph showing percent change in HR for subject 6 of the study.

Heart Rate (HR). Heart rate was monitored by the BVM with a photoelectric sensor placed on the left index toe and by the MEDAC System/3 with a different photoelectric sensor placed on the right index finger. Effects from onset of acute blood loss on heart rate vary by subject and by stage of shock, however data suggests hemorrhagic bleeding is generally accompanied by increased heart rates[5,6,7]. In the study this parameter increased by a mean of 3.62% (range −8 to 12 bpm) for all subjects reaching >450 ml blood draw as measured by the MEDAC System/3. Initial comparison to % ΔBI reveals a similar percent change but heart rate appears to be weaker in correlation to % TBV removed ($R^2=0.38$). In addition, a notable delay (~3 to 5 min latent phase shift) was observed from changes in % ΔHR relative to % ΔBI. This apparent delay has been noted in other studies suggesting increased heart rate may be a latent physiological response signaling the beginning of circulatory decompensation at levels 1 L of blood loss[3,7]. The HR data for subject 6 collected from the MEDAC System/3 can be seen graphically in FIG. 7.

During data collection some erratic changes were observed in the heart rate values calculated by the system. It was determined that there were two potential sources of this behavior. First, this early generation design proved to be sensitive to ambient lighting variations in the visible light spectrum. Second, the toes of some subjects were cold to the touch, suspected as a result of vasoconstriction from the body's natural temperature regulation mechanisms. This temperature effect was more prevalent in female subjects. Output from the MEDAC system appeared to be more stable across all subjects and may be attributable to use of a near infra-red photoelectric sensor, as well as alternate sensor placement on finger tip. In comparing heart rate values of the two systems, BVM outputs are within 2 bpm of the MEDAC system when signal strength is robust and can vary by 30 bpm when external factors create undesired noise.

Peripheral Blood Flow (PBF, PBF2, PH). Vasoconstriction causes variations in amplitude of the blood volume pulse wave which can be measured by photoelectric sensors. Reductions in peripheral blood flow are noted by a decrease in pulse wave amplitude which was measured by two separate systems. The BVM system measured peripheral blood flow of the left index toe; PBF and PBF2. The peak-to-peak amplitude (PBF) decreased during the blood draw period by a mean of −12% for the sub-set of all subjects <450 ml blood loss with no suspected noise during this period. (See Table 3) For this same sub-group, the root mean square (rms) amplitude (PBF2) decreased by −22%. The rms amplitude may provide insight into a beat-to-beat averaged trend of peripheral blood flow. Both values have significant variation in percent change from subject to subject at this low level of blood loss. The MEDAC System/3 measured the peripheral blood flow of the right ring finger. The pulse height (PH) decreased by −38% for the same sub-group and was more consistent in downward trend. In addition, subject 6 with greatest percent blood loss exhibited the greatest decrease in pulse height (−85%) of all subjects. Data from subject 6 for PBF2 is shown in FIG. 8 and for PH is shown in FIG. 9.

TABLE 3

% of Parameters Measured (450-500 ml blood draw)

| | Subjects | BVM | | | | MEDAC System/3 | | | | | |
|---|---|---|---|---|---|---|---|---|---|---|---|
| n | % TBV Removed | % BI (17sec avg) | % HR (120 sec avg) | % PBF (17sec avg) | % PBF2 (120 sec avg) | % HR (120 sec avg) | % PH (120 sec avg) | % SCR (120 sec avg) | % SCL (120 sec avg) | % ST (120 sec avg) | % R (120 sec avg) |
| 6 | 10.3% | 4.63% | 21.59% | −47.92% | −76.37% | 16.70% | −85.45% | −11.02% | 66.08% | 2.39% | 0.18% |
| 7 | 9.2% | 3.84% | 0.64% | −19.10% | −19.61% | 5.11% | −40.98% | −8.80% | 2.53% | −0.86% | −0.29% |
| 2 | 8.6% | 2.36% | −3.91% | −6.41% | −14.28% | 21.34% | −26.60% | 8.62% | −19.19% | 1.10% | 0.07% |
| 9 | 8.4% | 3.42% | −16.74% | 56.25% | 29.60% | −11.52% | 14.63% | −26.24% | −26.70% | −2.95% | 0.04% |
| 4 | 8.3% | 1.80% | −4.11% | 6.50% | 1.36% | −4.41% | −33.09% | −8.90% | −0.79% | −0.17% | −0.03% |
| 3 | 5.6% | 1.92% | 7.66% | −61.08% | −53.72% | 1.84% | −61.40% | −28.70% | 20.25% | −0.52% | 0.15% |
| | Mean | 2.99% | 0.85% | −11.96% | −22.17% | 4.84% | −38.82% | −12.51% | 7.03% | −0.17% | 0.02% |
| | Std Dev | 1.14% | 12.91% | 41.91% | 38.04% | 12.45% | 33.85% | 13.61% | 33.37% | 1.82% | 0.17% |
| | Pearson's | 0.75 | 0.20 | 0.19 | −0.05 | 0.38 | −0.10 | 0.53 | 0.26 | 0.40 | −0.21 |

Figure 10:
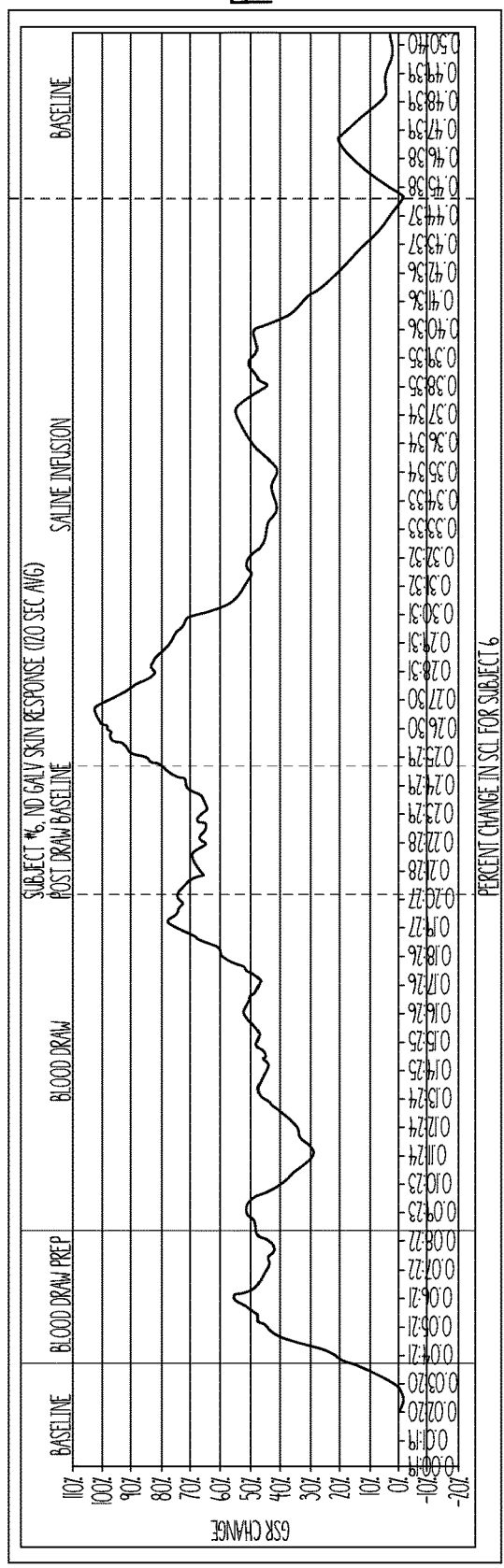
FIG. 10 is a graph showing percent change in SCL for subject 6 of the study.

Electrodermal Activity (SCL, SCR). Electrodermal conductance (commonly referred to as Galvanic Skin Reflex) is a compound measurement with two principal measurements SCL and SCR. The unit of measure for skin conductance level (SCL) is the micromho where larger values indicate a higher level of conductivity. The SCL value is expected to increase with greater activation of the sympathetic nervous system22. Mean values at baseline were 2.25 micromho's (consistent with typical normative values) and increased a mean of 21.3% for all subjects with >450 ml blood loss. When considering correlation to % TBV loss, some subjects demonstrated a decrease in SCL activity while the subject with highest blood loss (subject 6, 10.3% TBV loss) exhibited the greatest increase of 66%. The SCR values are relative in nature and have no formal units. The SCR values are generated by an amplifier circuit to monitor the rapid changes of phasic receptors which diminish very quickly. As a result, very little marked change in trend from baseline and throughout the blood draw period was observed. It was noted, however, that the SCR values monitored during the saline infusion period oscillated in a lower range than the blood draw period. The SCL response for subject 6 can be seen in FIG. 10.

Figure 11:
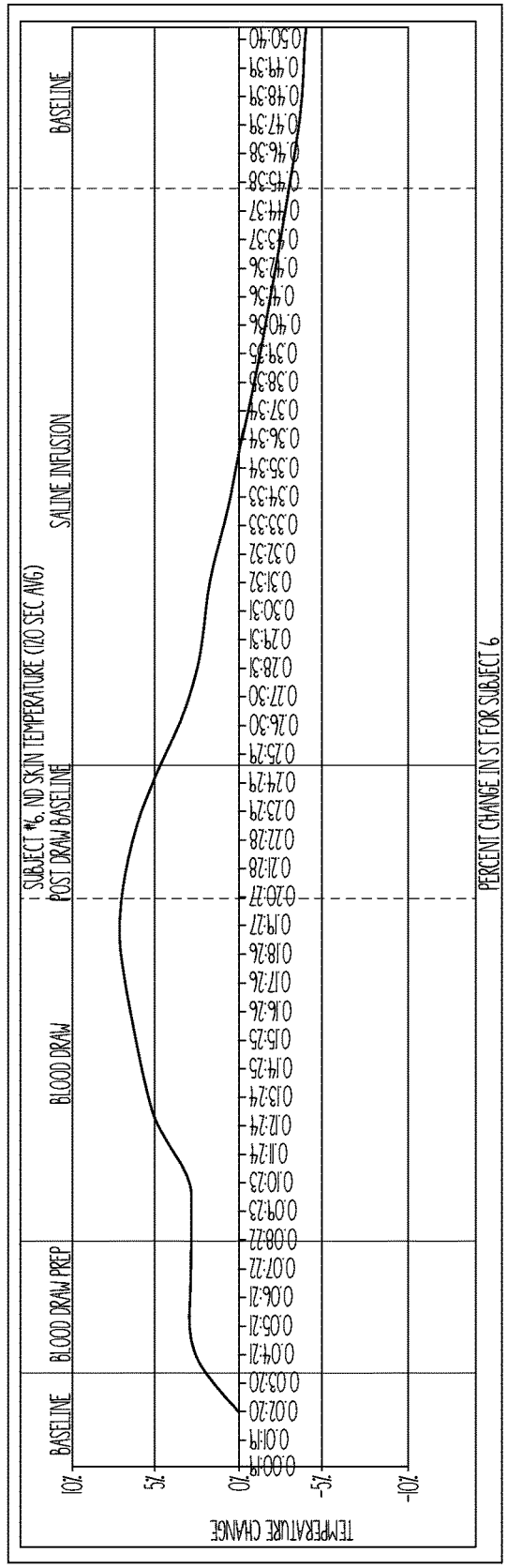
FIG. 11 is a graph showing percent change in ST for subject 6 of the study.

Skin Temperature (ST). Skin temperature was measured with a temperature sensitive semi-conductor sensor placed on the ring finger of the right hand. As a result of the anticipated peripheral vasoconstriction caused by blood loss, it was expected that skin temperature would decrease during the blood loss period. Several studies in the literature cite observed measurement variations in temperature of the toe to be clinically valid for shock and cardiac index assessment techniques[8,20]. In the study, the mean change in skin temperature increased 0.33% (range −2° to +2° F.) for all subjects with >450 ml blood loss. In subject 6 with the greatest percent TBV loss, skin temperature increased 2.4%, the greatest change measured for all subjects. Room temperature variations were not measured over the same time period but will be collected in future studies. The ST for subject 6 is shown in FIG. 11.

Respiration (R). Respiration was monitored using a force sensitive resistor placed around the subjects abdomen at the diaphragm. This sensor is able to display relative changes in breathing patterns but is unable to directly measure respiratory rate. Patterns in respiration were stable throughout the study for all subjects.

CONCLUSION

Vital signs monitoring of heart rate and blood pressure is not adequately sensitive enough to alert clinicians to mitigate risks of patients developing cardiovascular collapse since normal blood pressure is typically sustained up to levels of 30% blood loss. Despite the limited number of subjects tested to date, the results from the various parameters measured and initial algorithm simulation of the BVM Index indicate that an early detection mechanism for dependably alerting levels of blood loss between 500 and preferably 750 to 1000 ml is a clinically relevant proposition.

Results. All parameters were measured successfully and nine of ten subjects achieved >450 ml of blood loss. Manual blood loss and saline infusion were detected with some limitation from instances of artifact error and transient shifts of measured parameters in three subjects. Simulations of the initial algorithm for the BVM Index successfully identified both blood loss and saline infusion in 6 of 9 (67%) subjects reaching >450 ml in blood loss. The subject experiencing 10.3% TBV loss demonstrated the most definitive characteristics of peripheral blood flow decrease and corresponding BVM Index change.

In view of the foregoing results as well as results obtained from data from other studies, it is apparent that blood volume imbalances, i.e. both blood loss and intravascular fluid gains, can be detected by the method and system of the present invention and that, in particular, early blood loss detection of between 500 to 1000 ml (10 to 20% of TBV) can be detected such that clinicians can be timely alerted to enable them to take measures to mitigate the risks associated with and/or prevent patients from developing complete cardiovascular collapse.

In the preferred method of the present invention, effective early detection of between 10 and 20% blood loss in a subject can be achieved by measuring and monitoring as few as three of the subject's physiological parameters wherein the parameters include heart rate, electrical body impedance, skin temperature, perfusion index, peripheral blood flow and skin humidity. The preferred method includes obtaining baseline (i.e. patient resting in the supine position) measurements of these parameters from the subject which with the exception of the subject's heart rate are taken at one or more extremities of the subject, preferably the subject's thigh, forearm, calf, ankle, fingers and toes. The selected parameters are then monitored to detect changes from the baseline measurements that indicate blood volume imbalances. As indicated, the preferred extremities are the thigh, forearm, calf, ankle, fingers and toes. However, as used in the claims appended hereto extremities means any area of the body outside the thorax or thoracic region.

In a more preferred embodiment of the method of the present invention, a baseline blood volume index is computed from the baseline value measurements of each parameter to be monitored. This preferred embodiment of the invention further obtains real time value measurements of the parameters and then computes a real time blood volume index by inputting the baseline and real time values into an algorithm which considers the differences or changes between the baseline and real time value measurements. The algorithm includes coefficients for weighting each parameter so that each parameter is weighted equally in the blood volume index so that relevant changes in the trend of a parameter do not overshadow relevant trend changes in the other parameters. The current algorithm computing the blood volume index (BVI) is discussed in more detail above.

In addition, in the preferred embodiment, the blood volume index is then monitored (either automatically or manually) to determine whether a predetermined blood volume index threshold (typically set between 10 and 20% of the subject's TBV) is reached indicating potential bleeding. In a most preferred embodiment, the baseline BVI would be set at 100 and the threshold would be set at 85 so that a clinician would be alerted when the BVI reaches 85 which would indicate that the subject has lost 15% of his/her total blood volume (TBV).

As indicated above, the method of the present invention is also capable of detecting intravascular fluid increases, i.e. fluid gains, which can occur if the subject is administered too much saline solution. In this case, the system of the present invention can be set to detect such elevated intravascular fluid levels by setting the system to set off an alarm or signal when the subjects BVI reaches a threshold of 110 which would indicate a 10% increase in intravascular fluid levels.

Figure 12:
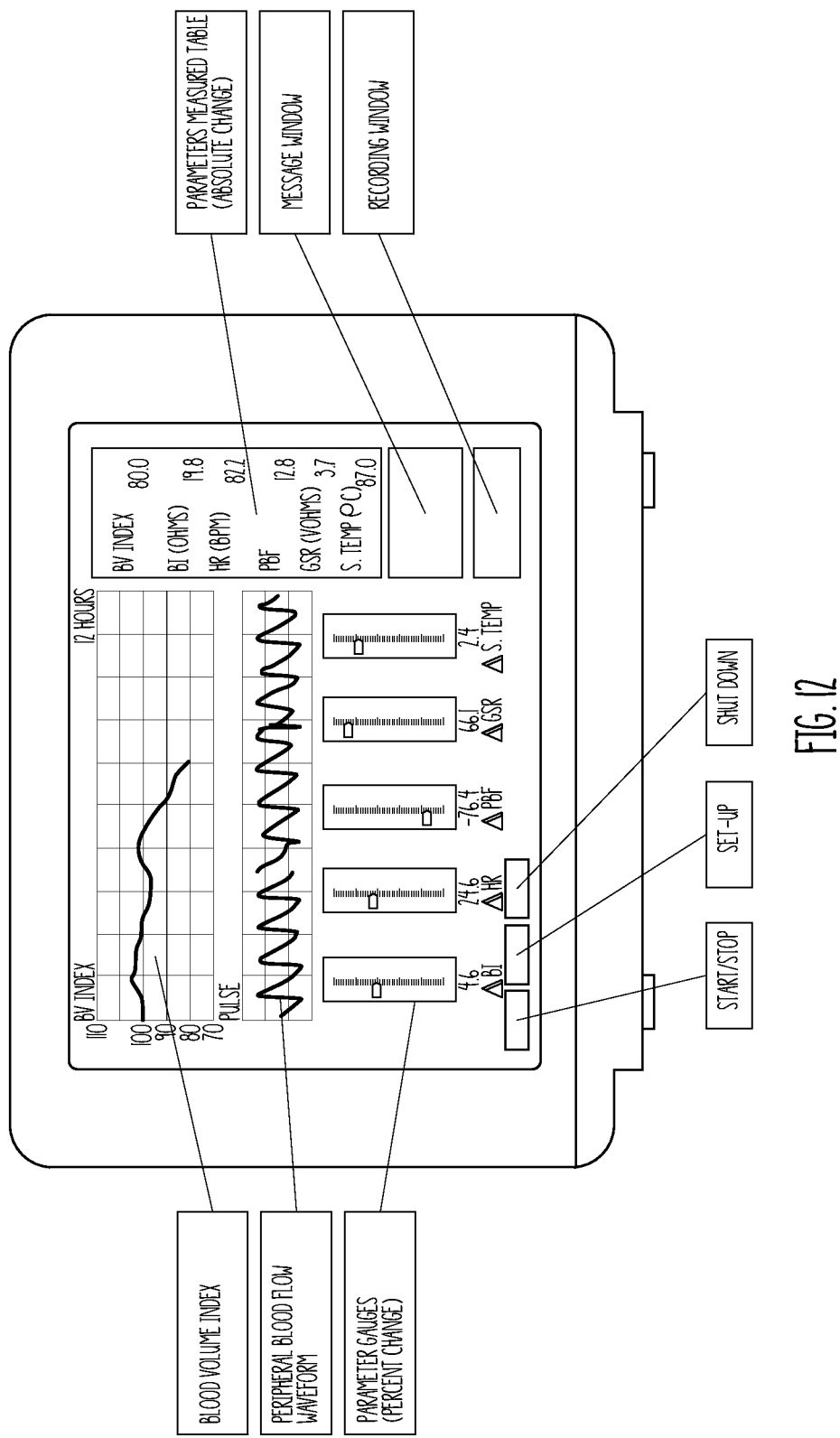
FIG. 12 is a front elevation view of a monitor of a system of the present invention.

The present invention also provides a monitoring apparatus or system for carrying out the method of the present invention. The preferred embodiment of the system monitors five parameters which are 1) bioimpedance 2) heart rate 3) skin temperature 4) skin humidity 5) peripheral blood flow. As set forth in FIG. 12, the five parameter measurements are displayed on a monitor screen in numeric unit form in the parameters measured table, as a percentage change in the parameter gauge display, and collectively compiled and computed to display an index in the blood volume index display.

Bioimpedance: Regional bioimpedance (BI) is measured across the forearm or calf to detect intravascular fluid changes. As blood flow to the extremity is reduced BI is expected to increase. As blood flow to the extremity is further reduced through vasoconstriction, BI will continue to increase as a result. BI is displayed in ohms within the parameters measured table as a numeric value and as a trend in the parameter dashboard for BI.

Heart Rate: Heart Rate (HR) is measured with a photoelectric sensor and displayed as beats per minute in the parameters measured table. Effects from the onset of blood loss on heart rate vary by subject but generally hemorrhagic bleeding is accompanied by an increased heart rate. Heart rate is displayed within the parameters measured table as a real-time numeric value and as a trend in the parameter dashboard for HR.

Peripheral Blood Flow: Peripheral Blood Flow (PBF) is the amplitude of arterial blood flow measured through the peripheral extremities. Blood loss causes variations in amplitude of the blood volume pulse wave which is measured by a photoelectric sensor. Reductions in peripheral blood flow are noted by a decrease in pulse wave. Peripheral blood flow is displayed within the parameters measured table as a real-time numeric value and as a trend in the parameter dashboard for PBF. While photoelectric sensors are currently used to measure PBF, better results may be obtainable by using the BI electrodes which should be more stable and less susceptible to patient movement. The PBF parameter may also be computed from a multitude of data within the signal, other than just amplitude, such as peak value, pulse width and the slope of the signal.

Humidity: Skin Humidity or Electrodermal conductance is also commonly referred to as Galvanic Skin Reflex (GSR). Skin humidity is expected to increase with greater activation of the sympathetic nervous system during blood loss. Humidity is displayed within the parameters measured table as a real-time numeric value and graphically in the parameter dashboard for GSR.

Temperature: Skin temperature is measured with a temperature sensitive semi-conductor sensor. Note: skin temperature may vary depending on environmental exposure. As a result of the anticipated peripheral vasoconstriction caused by blood loss, skin temperature will decrease. Skin temperature is displayed in degrees Fahrenheit within the parameters measured table as a real-time numeric value and as a trend in the parameter dashboard for S. TEMP.

Figure 13:
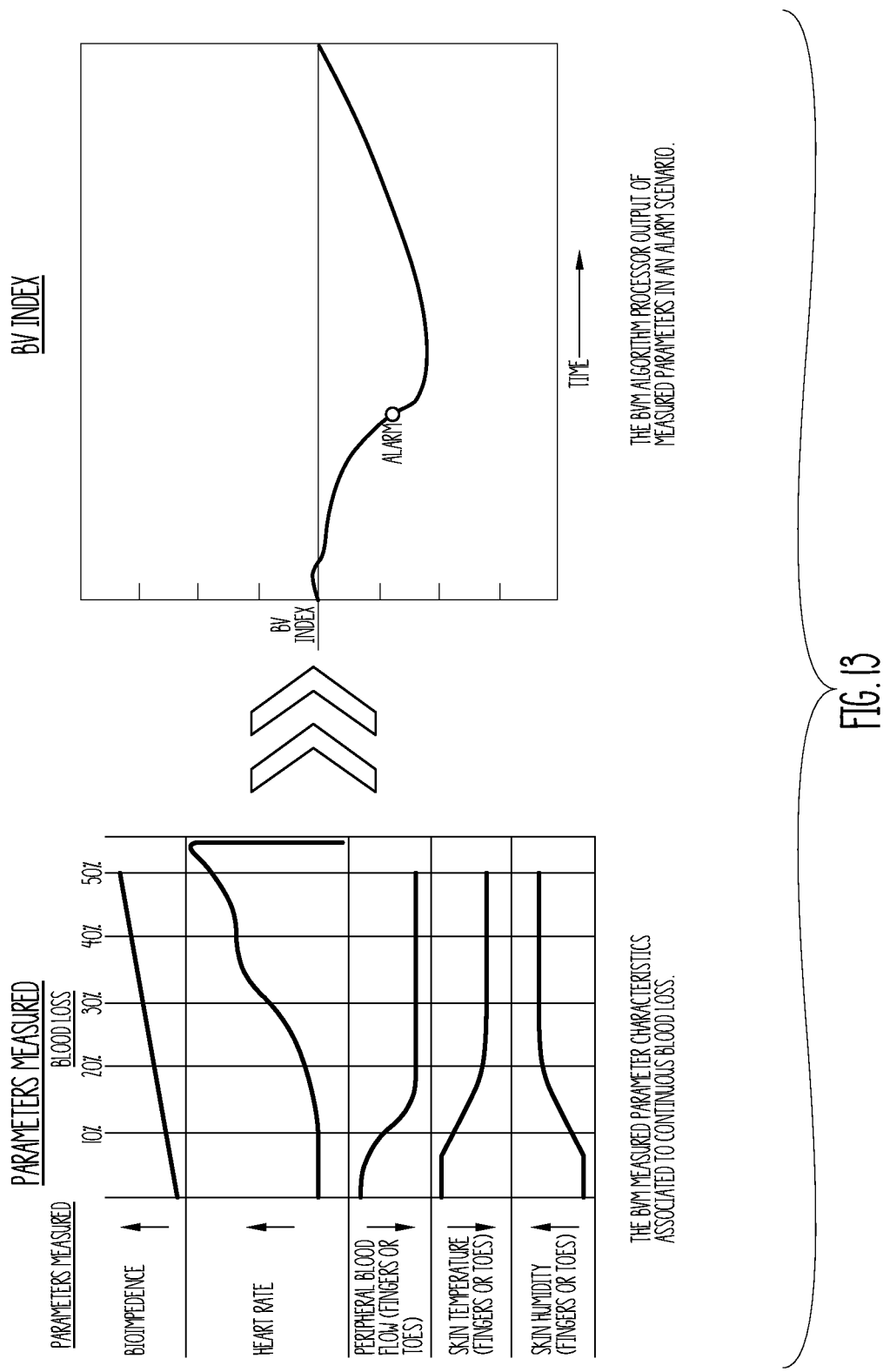
FIG. 13 illustrates a pair of graphs comparing five physiologic parameters measured by the system of the present invention with the BV Index generated by the present invention.

BV Index: The BV index is calculated by comparing baseline values of the five parameters to current patient conditions (See FIG. 13). A trend will be displayed reflecting sensor input changes from physiological response of the subject to their clinical status. The starting value of the Blood Volume (BV) Index is displayed as 100, and each parameter measured will be expressed as percent change relative to baseline values.

A trend in a stable condition or a condition with no change will show the BV Index line as a horizontal line.

A trend above the BV Index line could indicate fluids being added or recovery from blood loss.

A trend below the BV Index line would indicate blood loss.

Start: Selecting the start button will initiate patient monitoring and baseline values to establish the BV Index. The baseline values may take up to 4 minutes; the subject should remain still, the patient cable should not be disconnected. The Set Up button will be deactivated while the baseline values are being established.

Stop: Selecting the STOP button will pause/stop the monitoring data collection. The Set Up function will now become activated for selection.

Set Up: Selecting the Set Up button will prompt the Set Up window to appear on the monitor screen. From the Set Up window, Blood Volume Index (BV Index) time scales, Data Output options and Patient identification numbers may be changed. The Set Up button is only accessible when the monitor data recording is not running.

BV Index: Incremental time scales of 1 hour to 99 hours may be selected. The selected time scale will then be displayed on the BV Index monitor screen. The 3 hour scale is the default setting.

Bioimpedance Adjustment: Bioimpedance values displayed in the Parameter Gauges and BV Index displays may be adjusted to compensate for postural changes. A 3% adjustment is the default setting. Bioimpedance values displayed in the Parameter Measure Window are absolute real-time values and are unadjusted.

Data Output: In the Data Output window, one of the four selections may be made.

1. Store Data—Data will be stored in the system's internal memory only. No data will be streamed to the USB port.
   a. Erase Old Data—all data stored on the system's internal memory will be purged.
2. Live Streaming—Data will be streamed to USB port only. No data will be stored in the system's internal memory. (Default setting).
3. Offline Streaming—Data saved in the system's internal memory will be streamed to the USB port.

Patient Information: Unique 3 digit numeric patient identifier may be selected by scrolling up or down using the arrowed buttons. The patient identification number will be displayed in the recording window on the monitoring screen.

Shut Down—Selecting the Shut Down button will prompt the Shut Down window to appear on the screen allowing for confirmation OK to power off the system or cancel. An additional power switch is on the right—top side of the monitor which may be used for the same function.

Message Window: The message window displays prompts:
   Press START button to start monitoring.
   Baseline data capture is in progress. Please do not disconnect patient cable. (Baseline values may take up to 4 minutes)
   Baseline data capture is finished. Patient monitoring is in progress.

Recording Window: The recording window displays:
   Patient ID #: (Value is selected from the Set Up window. Data collected will be recorded under this number).
   Duration: (time elapsed in hours:minutes:seconds).
   Memory Usage: (memory storage capacity (percentage) elapsed).

Set Up
Monitor

Figure 14:
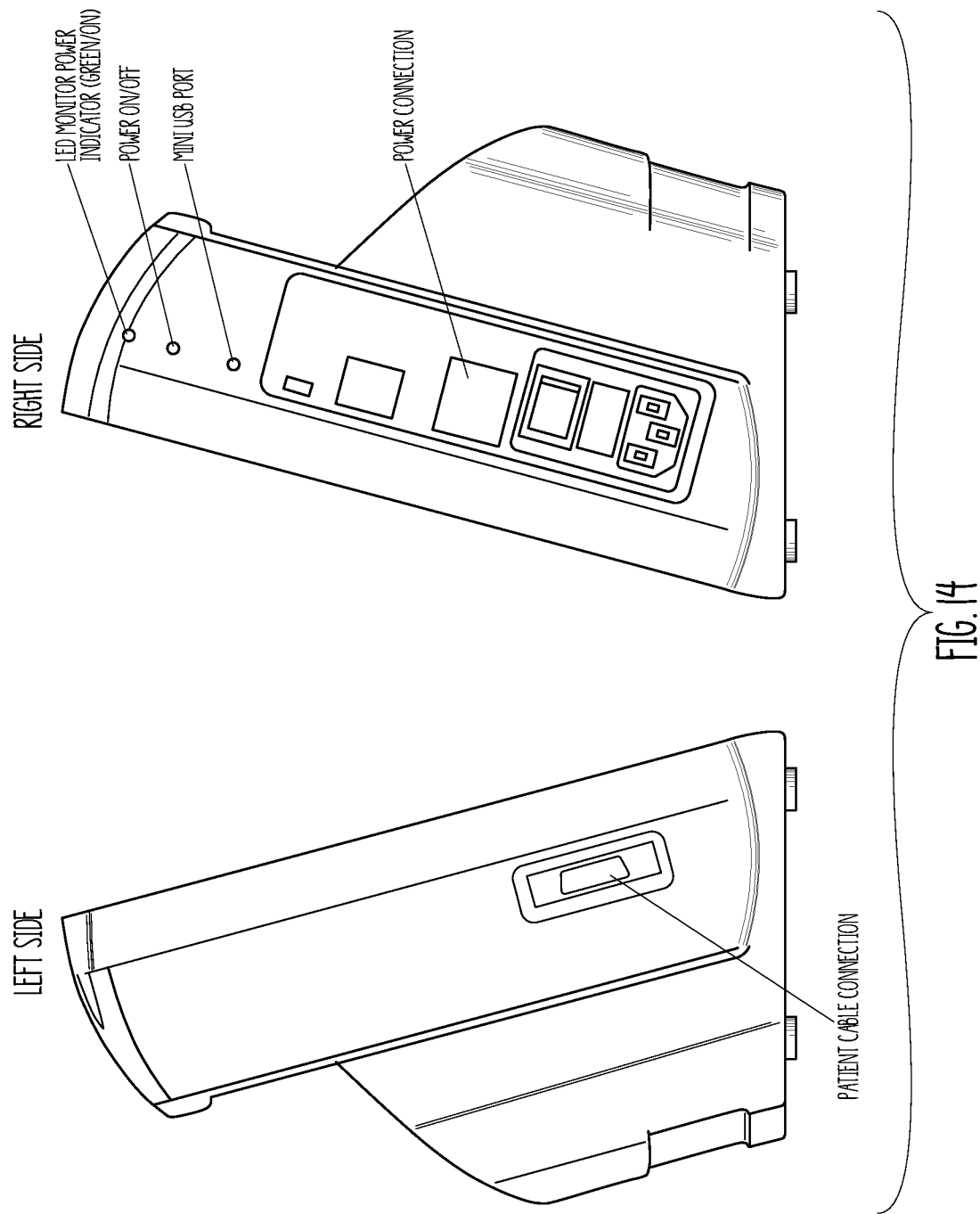
FIG. 14 illustrates left and right side elevation views of the monitor of FIG. 12.
Figure 15:
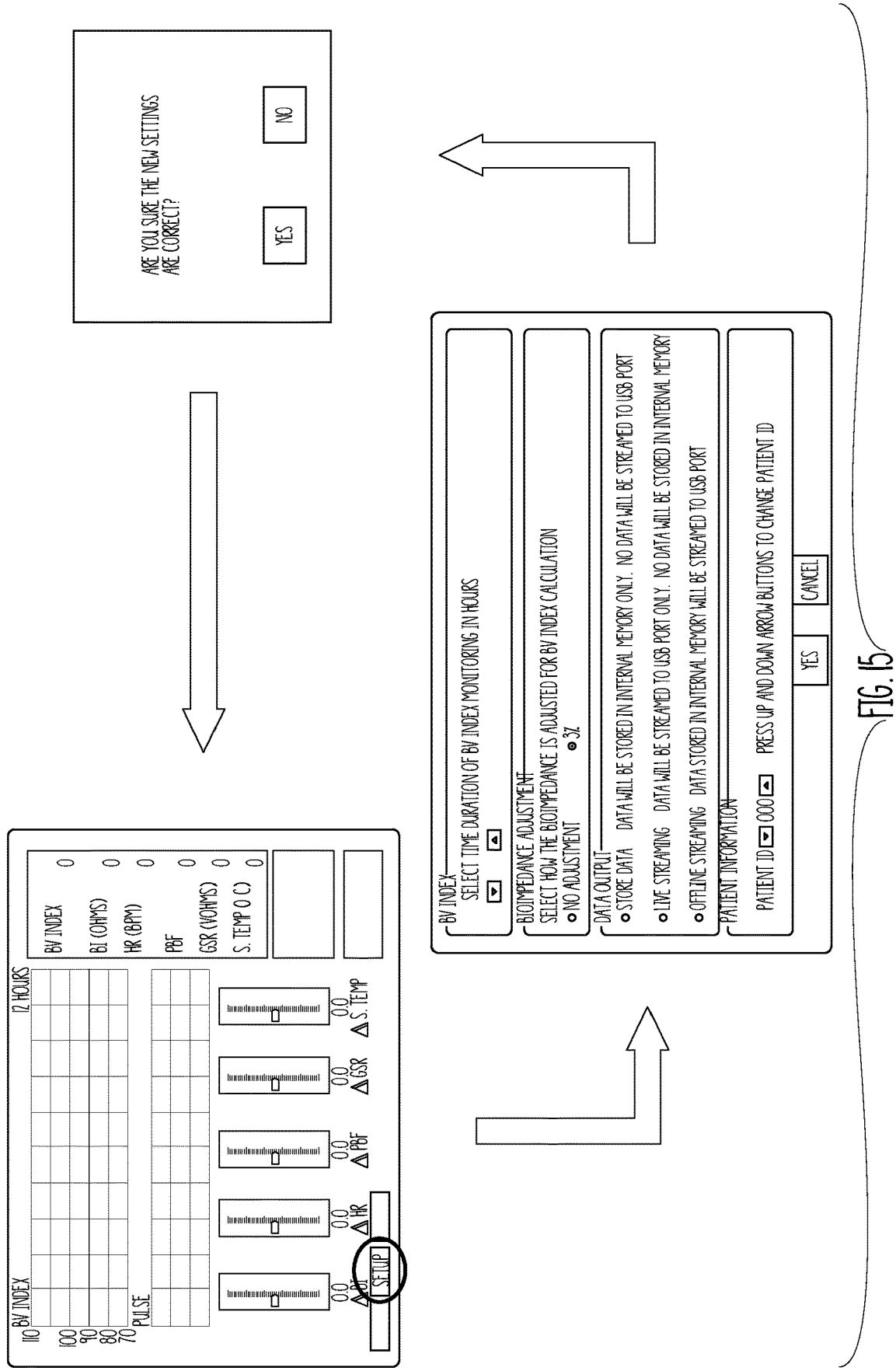
FIG. 15 illustrates screen shots which appear on the monitor of FIG. 12 during setup.

The system is set-up for data collection by following the steps in the sequence below:
1. Connect the power cable to the appropriate socket on the right side of the monitor (FIG. 14).
2. Attach the patient cable to the lower left side of the monitor (See FIG. 14).
3. The USB cable from the device may be connected to a computer with data collection software.
4. Press the power button labeled ON/OFF. A green LED light will be illuminated to confirm power supply to the monitor (See FIG. 14).
5. Selecting the Set Up button from the monitoring screen will allow changes to (See FIG. 15):
   a) BV Index time scale display.
   b) Bioimpedance Adjustment values.
   c) Data Output.
   d) Patient Information.
Once setting changes are complete, select the OK button. A confirmation window will appear to verify settings. By selecting Cancel, original settings will be returned.

Figure 16A:
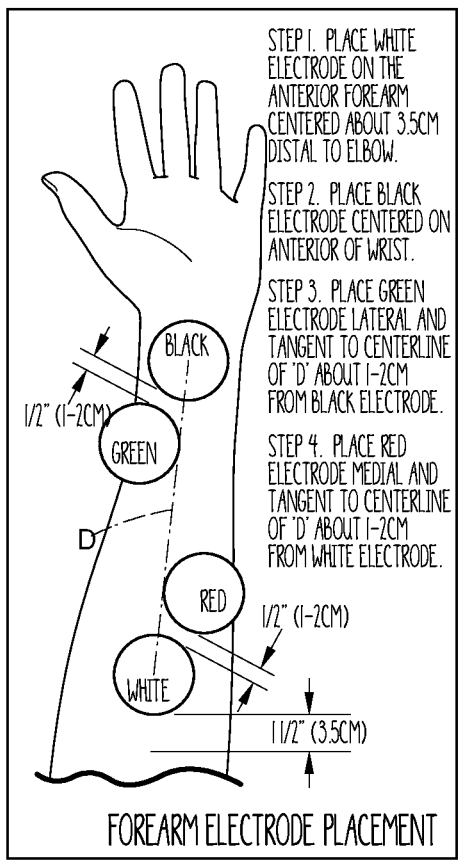
FIG. 16a is a side view showing forearm electrode placement.
Figure 16B:
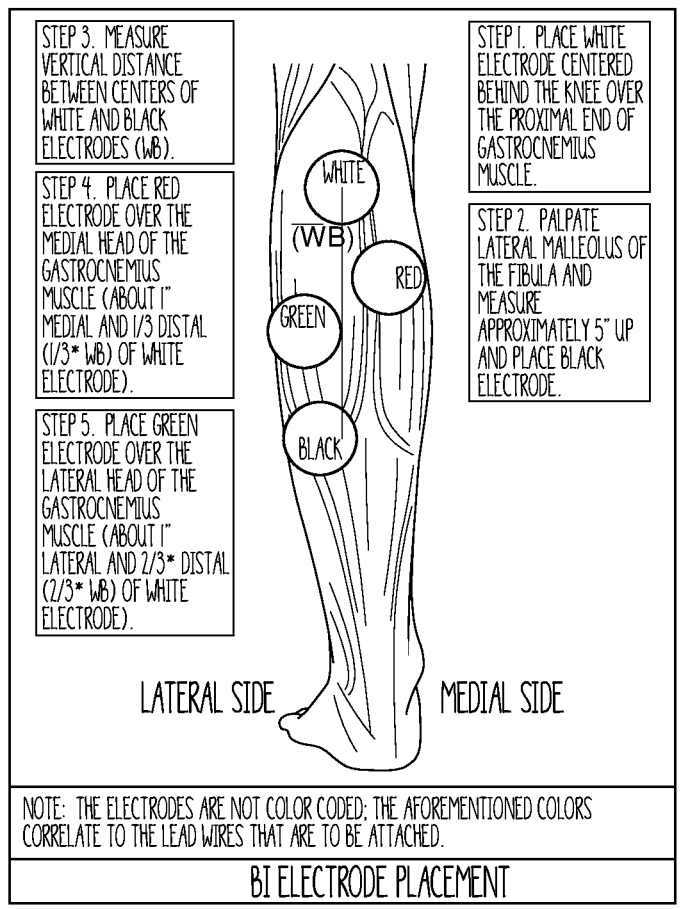
FIG. 16b is a side view showing BI electrode placement.
Figure 17:
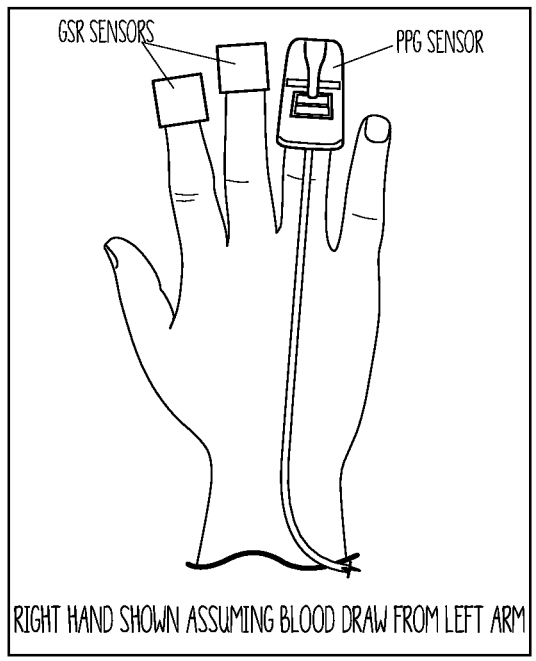
FIG. 17 is a side view showing sensor placement on the fingers.

Sensor Placement
1. Prep the area with an alcohol swab, apply the four self-adhesive electrode pads to either the forearm or calf (See FIG. 16a or FIG. 16b).
2. Connect the colored patient cable leads to the appropriate electrode (See FIG. 16a or FIG. 16b).
3. The patient cable consists of 3 sensors, a PPG sensor and 2 GSR sensors. Opposite to the arm identified for the blood draw; place the PPG sensor onto the 3rd finger ensuring the sensor is correctly aligned with the finger nail icon on the PPG sensor. The GSR sensors are secured onto the index and 2nd finger pads of the same hand as the PPG sensor (See FIG. 17).

The above-described embodiments of methods and apparatus for detecting blood loss and intravascular fluid gains of a mammalian subject are exemplary only. The following claims are not intended to be limited to these exemplary embodiments. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

REFERENCES

1. Little, R, Kirkman, E, Driscoll, P, Hanson, J, Mackay-Jones, K. Preventable Deaths after Injury: Why are the Traditional "Vital" Signs Poor Indicators of Blood Loss. Journal of Accident and Emergency Medicine 1995, 12:1-14.
2. Ryan K, Batchinsky A, McManus J, Rickards C, Convertino V. Changes in Pulse Character and Mental Status Are Late responses to Central Hypovolemia. Prehospital Emergency Care; April-June 2008; 12, 3; ProQuest Nursing & Allied Health Source: 192-8.
3. Soller B, Ryan K, Rickards C, Cooke W, Yang Y, Soyemi O, Crookers B, Heard S, Convertino V. Oxygen saturatin determined from neep muscle, not thenar tissue, is an early indicator of central hypovolemia in humans. Crit Care Med 2008 Vol. 36, No. 1: 176-82.
4. U. Yetkin, Yiirekli, A. Gürbüz: Revision for postoperative bleeding: timing and decision making. The Internet Journal of Thoracic and Cardiovascular Surgery. 2009 Volume 13 Number 1. DOI: 10.5580/16c6
5. Gutierrez, G, et. al. Clinical Review: Hemorrhagic shock. Critical Care 2004, 8:373-381.
6. Wilson, M, et. al. Diagnosis and Monitoring of Hemorrhagic Shock During the Initial Resuscitation of Multiple Trauma Patients: A Review. Journal of Emergency Medicine, Vol. 24, No. 4, pp. 413-422, 2003.
7. Garrioch, M. The body's response to blood loss. Vox Sanguinis, 87 (Suppl 1), S74-S76, 2004.
8. Ridling D, Kroon L. Comparing Three Methods of Assessing Peripheral Perfusion in Critically Ill Children. Continuing Nursing Education Series. Pediatric Nursing/January-February 2009. Vol. 35/No. 1: 11-5, 42.
9. Selvaraj N, Scully C, Shelley K, Silverman D, Chon K. Early Detection of Spontaneous Blood Loss using Amplitude Modulation of Photoplethysmogram. Conf Proc IEEE Eng Med Biol Soc. 2011; 2011:5499-502.
10. Kosowsky J, Han J, Collins S, McAfee A, Storrow A. Assessment of Stroke Index Using Impedance Cardiography: Comparison with Traditional Vital Signs for Detection of Moderate Acute Blood Loss in Healthy Volunteers. ACAD Emerg Med: August 2002, Vol. 9, No. 8: 775-80.
11. Cai Y, Holm S, Jenstrup M, Strømstad M, Eigtved A, Warberg J, Højgaard L, Friberg L, Secher N H. Electrical admittance for filling of the heart during lower body negative pressure in humans. J Appl Physiol. 2000 October; 89(4):1569-76.
12. Krantz T, Cai, Y, Lauritsen T, Warberg J, Secher N H. Accurate monitoring of blood loss: thoracic electrical impedance during hemorrhage in the pig. Acta Anaesthesiol Scand. 2000; 44(5):598-604.

13. Perko M J, Jarnvig I L, Højgaard-Rasmussen N, Eliasen K, Arendrup H. Electric Impedance for Evaluation of Body Fluid Balance in Cardiac Surgical Patients. Journal of Cardiothoracic and Vascular Anesthesia. 2001; 15(1): 44-8.
14. Cai Y, Zimmerman A, Ladefoged S, Secher N H. Can Haemodialysis-Induced Hypotension Be Predicted? Nephron 2002; 92(3):582-8.
15. Perko G, Payne G, Secher N H. An indifference point for electrical impedance in humans. Acta Physiol Scand. 1993 June; 148(2):125-9.
16. Scheltinga Marc, Jacobs D, Kimbrough T, and Wilmore D. Alterations in Body Fluid Content Can be Detected by Bioelectrical Impedance Analysis. J of Surgical Research: vol. 50, No. 5, May 1991.
17. Matzen S, Perko G, Groth S, Friedman D B, Secher N H. Blood volume distribution during head-up tilt induced central hypovolaemia in man. Clin Physiol. 1991 September; 11(5):411-22.
18. Ishibe S, Peixoto A J. Methods of assessment of volume status and intercompartmental fluid shifts in hemodialysis patients: implications in clinical practice. Semin Dial. 2004 January-February; 17(1):37-43.
19. Kushner R, Gudivaka R, Schoeller D. Clinical characteristics influencing bioelectrical impedance analysis measurements1-3. The American Journal of Clinical Nutrition. 1996; 64(suppl): 423S-7S.
20. Isben Bjorn. Treatment of shock with Vasodilators Measuring Skin Temperature on the Big Toe. Diseases of the Chest: vol. 52, No. 4, October 1967. 425-428.
21. Selvaraj N, Shelley K, Silverman D, Stachenfeld N, Galante N, Florian J, Mendelson Y, Chon, K. A Novel Approach Using Time-Frequency Analysis of Pulse-Oximeter Data to Detect Progressive Hypovolemia in Spontaneously Breathing Healthy Subjects. IEEE Transactions on Biomedical Engineering. Vol. 58. No. 8, August 2011: 2272-9.
22. Fowles, D. C. et. Al. Committee report: Publication recommendations for electrodermal measurements. Psychophysiology, 19(3), 232-239. 1981.
23. Alian A A, Galante N J, Stachenfeld N S, Silverman D G, Shelley K H. Impact of Central Hypovolemia on Photoplethysmographic Waveform Parameters in Healthy Volunteers. Part 1: Time Domain Analysis. Journal of Clinical Monitoring and Computing (2011) 25: 377-385.
24. Alian A A, Galante N J, Stachenfeld N S, Silverman D G, Shelley K H. Impact of Central Hypovolemia on Photoplethysmographic Waveform Parameters in Healthy Volunteers. Part 2: Frequency Domain Analysis. Journal of Clinical Monitoring and Computing (2011) 25: 387-396.

I claim:

1. A noninvasive method for detecting blood volume imbalances in a mammalian subject comprising:
   noninvasively obtaining baseline physiologic value measurements, over a period of time from the subject, of at least three of physiological parameters selected from the group including heart rate, electrical body impedance, skin temperature, perfusion index, peripheral blood flow, and skin humidity; and
   with at least one integrated circuit:
      computing, using the baseline physiologic value measurements, a starting value blood volume index which indicates 100% of the subject's normal total blood volume;
      displaying the starting value blood volume index on an electronic display;
      after computing said starting value blood volume index, noninvasively obtaining real time physiologic value measurements of the selected at least three physiological parameters;
      computing, with an algorithm, a real time blood volume index of the subject based upon difference values calculated between the baseline physiologic value measurements and corresponding real time physiologic value measurements, wherein the algorithm includes coefficients for weighting each difference value used to compute the real time blood volume index;
      displaying the real time blood volume index on the electronic display; and
      displaying, on the electronic display, changes in the real time blood volume index, from the starting value blood volume index, that indicate blood volume imbalances as low as 10% of the subject's normal total blood volume.

2. The method as claimed in claim 1, wherein the period of time is up to 4 minutes.

3. The method as claimed in claim 1, wherein the baseline and real time physiologic value measurements of electrical body impedance, skin temperature, peripheral blood flow, and skin humidity are taken at one or more extremities of the subject.

4. The method of claim 1, wherein baseline measurements of at least four physiological parameters from the group consisting of heart rate, electrical body impedance, skin temperature, perfusion index, peripheral blood flow, and skin humidity are obtained.

5. The method of claim 1, wherein baseline measurements of at least five physiological parameters from the group consisting of heart rate, electrical body impedance, skin temperature, perfusion index, peripheral blood flow, and skin humidity are obtained.

6. The method of claim 1, further comprising determining whether changes in the real time blood volume index reach a predetermined change threshold.

7. The method of claim 6, further comprising sounding or signaling an alarm when the predetermined change threshold is reached.

8. The method of claim 1, wherein the subject's starting value blood volume index corresponds to a reading of 100 on the electronic display.

9. The method of claim 8, wherein the electronic display displays a blood volume index range between 110 and 60, and wherein a reading of 85 indicates potential blood loss of about 15% in the subject and a reading of 110 indicates an increase of about 10% in the subject's intravascular fluid levels.

10. The method of claim 8, wherein the electronic display displays a blood volume index range between 140 and 45, and wherein a reading of 45 indicates potential blood loss of about 55% in the subject and a reading of 140 indicates an increase of about 40% in the subject's intravascular fluid levels.

11. The method of claim 8, further comprising determining whether the real time blood volume index reaches a predetermined blood volume index threshold.

12. The method of claim 1, wherein extremities of the subject at which the baseline and real time physiologic value measurements are taken include the subject's thigh, forearm, ankle, calf, fingers, or toes, or any combination thereof.

13. The method of claim 1, further comprising determining whether the real time blood volume index reaches a predetermined blood volume index threshold.

14. The method of claim 13, further comprising sounding or signaling an alarm when the predetermined blood volume index threshold is reached.

15. An apparatus for noninvasively detecting blood volume changes in a mammalian subject, the apparatus comprising:
   an electronic display;
   a number of noninvasive sensors configured to communicate with said electronic display and the subject to obtain baseline physiologic value measurements and real time physiologic value measurements from the subject; and
   at least one integrated circuit, operably connected with the noninvasive sensors and configured to:
      compute, using an algorithm, a real time blood volume index based upon difference values calculated between the baseline physiologic value measurements and corresponding real time physiologic value measurements, wherein the baseline physiologic value measurements and the real time physiologic value measurements are derived from at least three physiological parameters selected from the group including heart rate, electrical body impedance, skin temperature, perfusion index, peripheral blood flow, and skin humidity, and wherein the algorithm includes coefficients for weighting each difference value used to compute the real time blood volume index; and
      display the real time blood volume index on said electronic display, wherein the electronic display is initially set to display a starting value blood volume index which indicates 100% of the subject's normal total blood volume, and wherein the displayed real time blood volume index is capable of indicating a blood volume change in the subject as low as 10% of the subject's starting value blood volume index.

16. The apparatus of claim 15, wherein said noninvasive sensors include sensors capable of obtaining the real time and the baseline physiologic value measurements at one or more extremities of the subject.

17. The apparatus of claim 15, wherein the noninvasive sensors comprise a plurality of electrodes disposed on a thigh band, an ankle band, or an arm band.

18. The apparatus of claim 15, wherein the noninvasive sensors comprise a plurality of electrodes disposed in a blood pressure cuff.

19. The apparatus of claim 15, wherein the noninvasive sensors comprise a plurality of independently positionable electrodes.

20. The apparatus of claim 15, further comprising an alarm which is activated when the real time blood volume index reaches a predetermined real time blood volume index threshold.

* * * * *